United States Patent

[11] 4,299,482
[45] Nov. 10, 1981

Task

[54] MEASUREMENT OF WINDSCREEN DISTORTION USING OPTICAL DIFFRACTION

[75] Inventor: Harry L. Task, Montgomery County, Ohio

[73] Assignee: The United States of America as represented by the Secretary of the Air Force, Washington, D.C.

[21] Appl. No.: 90,383

[22] Filed: Nov. 1, 1979

[51] Int. Cl.³ ............................................... G01B 9/00
[52] U.S. Cl. .................................................... 356/124
[58] Field of Search ....................... 356/124, 125, 347; 350/162 R, 162 SF

[56] References Cited

U.S. PATENT DOCUMENTS

| | | | |
|---|---|---|---|
| 1,590,532 | 6/1926 | Lenouvel | 356/124 |
| 3,418,626 | 12/1968 | Farr et al. | 350/162 R |
| 3,614,232 | 10/1971 | Mathisen | 356/71 |
| 3,619,064 | 11/1971 | Brooks et al. | 356/347 |
| 3,912,395 | 10/1975 | Voggenthaler | 356/124 |

OTHER PUBLICATIONS

Heiling, G. M., and L. T. Lemke, "Lens Magnification Measuring System", IBM Technical Disclosure Bulletin, vol. 14, No. 5, Oct. 1971.

*Primary Examiner*—Conrad J. Clark
*Attorney, Agent, or Firm*—Donald J. Singer; Casimer K. Salys

[57] ABSTRACT

A measurement apparatus and method for detecting, resolving and quantifying the distortion caused by a relatively large region of a distorting optically transparent medium. A precisely defined pattern is viewed through the transparent medium to introduce the distortion effects. The altered pattern is photographically recorded in thin film transparency format. A beam of coherent luminous energy projected through the transparency, once focused, produces a Fraunhofer diffraction pattern which is the Fourier transform of the original pattern. Conventional distortion characteristics in the Fourier domain appear in a form more amenable to quantification and analysis. The character and magnitude of the distortion is readily ascertained by comparing the transforms of distorted and undistorted patterns, yielding quantitative data comparable to conventional distortion effects in terms of grid line slop and lens factor.

4 Claims, 7 Drawing Figures

MEASUREMENT OF WINDSCREEN DISTORTION USING OPTICAL DIFFRACTION

RIGHTS OF THE GOVERNMENT

The invention described herein may be manufactured and used by or for the Government of the United States for all governmental purposes without the payment of any royalty.

BRIEF SUMMARY

The present invention is directed to measurement apparatus and method by which the distortion effects in an optically transparent medium are detected, resolved and quantified. A precision pattern consisting of black and white lines is observed and recorded through the medium, with the alterations caused by the medium distortion inherently present. When a thin transparency of the recorded image is placed into the path of a coherent luminous energy beam, and the pattern generated thereby is focused, the transparency pattern undergoes an optical Fourier transform into a Fraunhofer diffraction pattern.

The shape and distribution characteristics of the transformed pattern present the distortion parameters in a form which is readily amenable to quantification and comparison. Convention distortion characteristics such as grid line slope and lens factor appear as quantifiable geometric dimensions in the diffraction pattern. Furthermore, the Fraunhofer diffraction pattern characterization is not limited to presenting maximum values, but rather depicts the total distribution of the distortion.

The degree of the distortion is always ascertained by comparing the transformed patterns with the distortion effects to a pattern obtained without the presence of a distorting medium. In the alternative, the comparison may be performed by deconvolving the pattern without the medium with the pattern containing distortion effects.

DETAILED DESCRIPTION

The optical distortion introduced by a large optically transparent medium has heretofore been difficult to quantify. In most cases distortion quantification parameters such as grid line slope and lens factor are ascertained by manual inspection of patterns, for instance 1 inch white grid on a black background, distorted as a result of being observed through the optical medium.

An exemplary optically transparent medium is the wind-screen of a military aircraft, being both thick and curvilinearly complex yet restricted in distortion to the tolerances allowed by the weapons system which must be aligned through it. It is to this specific application that the embodying apparatus and method are directed. Nevertheless, the broad underlying concept is significantly more encompassing.

Inspection of windscreens in the manner of the art, i.e. visual analysis of patterns accurately photographed through the windscreen, is tedious and highly susceptible to subjective errors. Furthermore, this technique is not readily amenable to quantification with pass-fail type thresholds for purposes of production inspection or comparison.

The invention in its broad sense overcomes these deficiencies by using measurement apparatus and method which transform the distorted pattern recorded in conventional manner, i.e. through the windscreen, into its optical Fourier domain equivalent, where pattern distortions are readily quantified into measurable characteristics.

Figure 1:
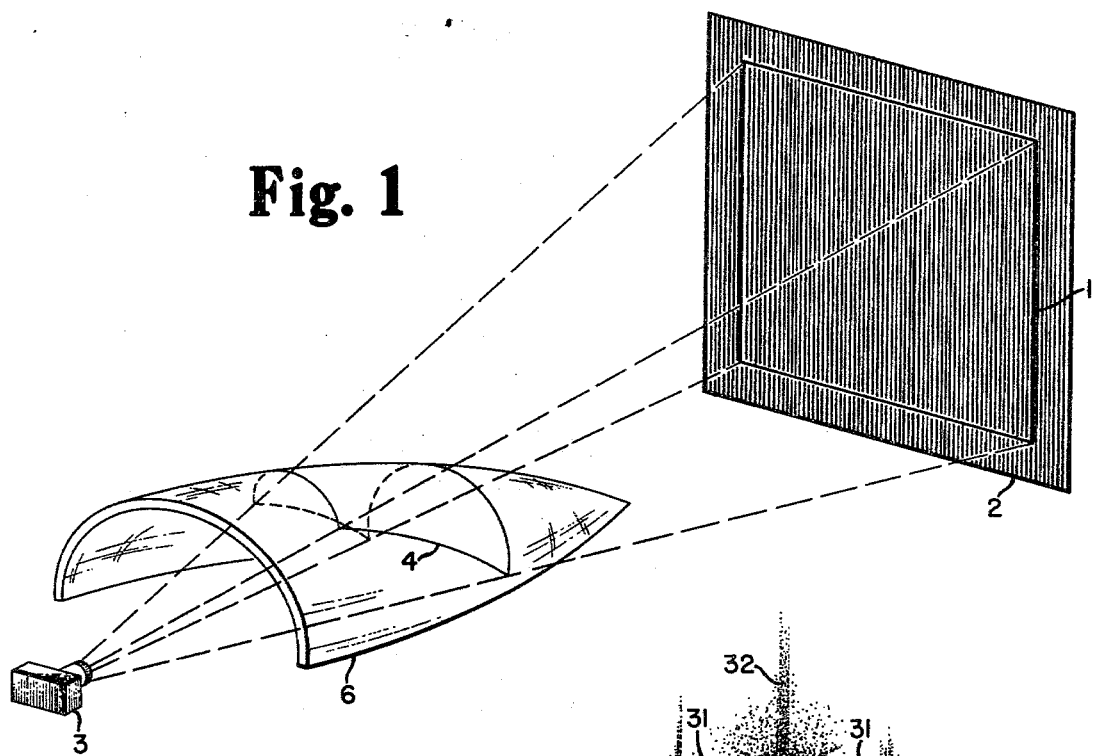
FIG. 1 is a perspective schematic of a pattern being photographically recorded through a distorting windscreen.

As was noted in the foregoing, the invention is embodied in measurement apparatus used to detect distortion over a large optical area encompassing a complex curvilinear surface. FIG. 1 of the drawings schematically depicts the first element of the apparatus and process, where segment 1 of accurate, fine line pattern 2 is photographically recorded by camera 3 through section 4 of intervening windscreen 6. The image recorded by camera 3 can be in a negative or slide transparency format, as long as the high contrast of the pattern is retained in the transparency between the adjacent transparent and opaque bar segments. Furthermore, since the recorded image is to perform the function of a diffraction grating, the transparency must be thin and must contain an accurate reproduction of the viewed image. Naturally, bar pattern 2 itself must be accurate. Though adjacent contrasting bars may be unequal in width, their relative size must be consistent over the whole pattern.

Figure 2:
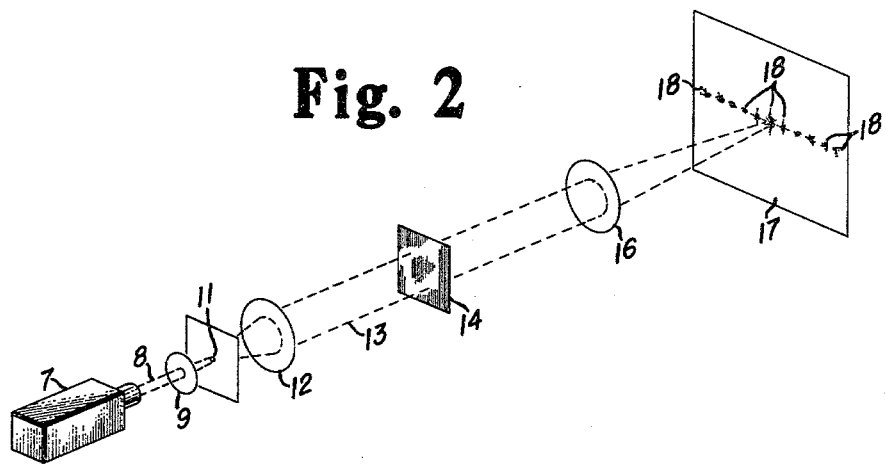
FIGS. 2 and 3 schematically depict the apparatus used to generate a Fraunhofer diffraction pattern from a photographic transparency.

The transparency recorded in the manner described is then inserted into the apparatus depicted in FIG. 2. As shown, laser 7 projects coherent light beam 8 through a spatial filter, having lens 9 and aperture 11, to remove fringe effects. The beam is collimated by lens 12 into broad beam 13. The expanded beam is projected through transparency 14 and focused by lens 16 at Fraunhofer diffraction plane 17. If beam 13 is collimated in the manner described, the distance between lens 16 and plane 17 is equal to the focal length of lens 16. Otherwise, the lack of collimation dictates that lens 16 and plane 17 be relocated accordingly. A further variation, which may be recognized by those skilled in the art, permits the placement of transparency 14 immediately behind lens 16 without altering the fundamental relationships of the patterns.

Figure 3:
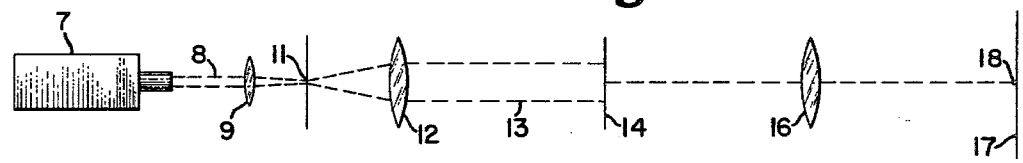

As noted, the transformation of the bar pattern into its Fraunhofer diffraction pattern equivalent is tantamount to performing an optical Fourier transform. As such, the distortion information contained in the distorted bar pattern of transparency 14 is now represented in a different domain, appearing generally as a row of luminous, extended points. The size, shape and location of points 18 at plane 17 are, as will become apparent hereinafter, quantitative indicators of specific distortion characteristics. Comparative magnitudes of the various distortion parameters are obtained by comparing the point characteristics to those created with a standard transparency, namely one recorded without the presence of windscreen 6. A schematic side view of the same apparatus appears in FIG. 3.

Figure 5:
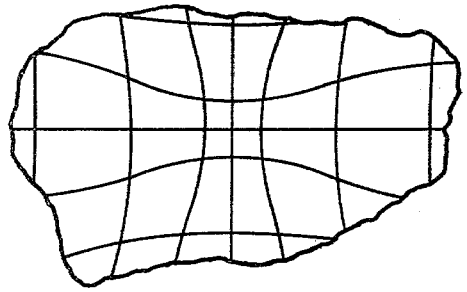
FIGS. 4 and 5 schematically show distortion phenomena known as grid line slope and lens factor, respectively.
Figure 4:
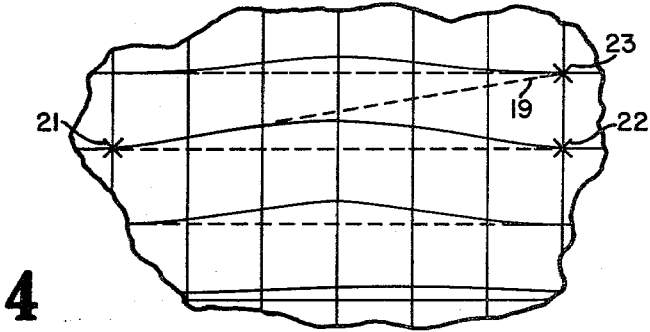

To recognize the principle characteristics contributing to windscreen distortion, inquiry is directed to FIGS. 4 and 5. The grid line slope effect is shown in FIG. 4 while lens factor (otherwise known as magnification or minification factor) effects are depicted in FIG. 5. The distortion in both figures is accentuated and shown within a grid pattern for added clarity. Conventionally, grid line slope is quantified by measuring the maximum slope of any curved grid line. In terms of FIG. 4, its measure is the slope of dashed line 19, for point 21, defined by the triangle within points 21, 22 and 23. As depicted it is approximately 1 in 6.

The pattern distortion appearing in FIG. 5 is generally classified in terms of lens factor. Quantification consists of a length comparison between the sides of a normal, undistorted cube and that altered by the windscreen distortions.

As shown in FIGS. 4 and 5 the two principal contributors to distortion are separate. Normally, the two coexist. Recognizing this concurrency, and the tens of thousands of grids in a normal pattern, the likelihood of having labor intensive and subjective contributors to error becomes readily apparent.

Figure 6:
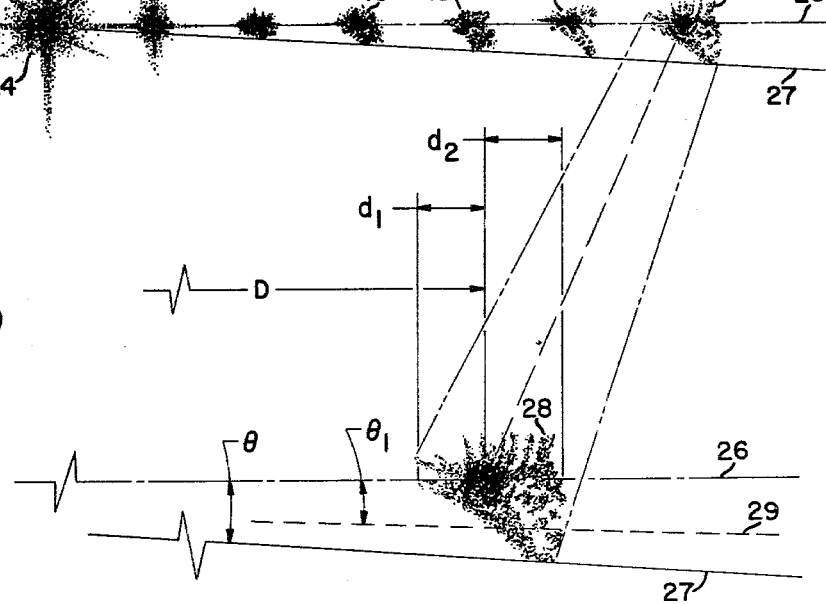
FIG. 6 is a schematic of the Fraunhofer diffraction pattern when magnified.

A segment of the Fraunhofer diffraction pattern is shown magnified in FIG. 6. Since the luminous energy extended points, generally designated 18, are symmetrically distributed about center point 24 along common center line 26, only half the transformed pattern need be considered. In addition to line 26, radially projecting line 27 has been inserted, extending from center point 24 to tangents with each point of luminous energy in the pattern. Center line 26 and projection line 27 define an angle $\theta$, clearly shown in the enlarged auxiliary view of point 28 and its immediate surroundings. The dimensions designated $d_1$ and $d_2$, in the auxiliary view, define the lateral excursions of luminous energy point 28 on center 26, while D is the distance from center point 24 to the center of point 28 on line 26 if no distortion is present.

Conventional grid line slope distortion appears in the Fourier domain of FIG. 6 as tangential digressions of points 18, most visible in large point 28, from a balance about center line 26. Since the angle $\theta$ is tangent to the greatest angular excursion of point 28, it corresponds to the maximum grid line slope distortion in the area of the windscreen undergoing analysis. The distribution of this distortion phenomenon is proportional to the luminous energy intensity along radially projecting lines at angles less than $\theta$, such as line 29 at angle $\theta_1$.

Lens factor type distortion is related to the radially directed spread of point 28. More specifically, the lens factor on center line 26 is defined by the relationships:

minification factor $= (D - d_1)/D$
magnification factor $= (D + d_2)/D$.

The width of point 28 along radial projections other than center line 26, for instance line 29, is similarly quantifiable into lens factor characteristics.

Based on the foregoing, automated quantification of the two distortion parameters is performed by taking radial and tangential slit scans of points such as 28. The data obtained during such scans, once normalized and calibrated, presents a distribution of grid line slope and lens factor. Normalization contemplates a difference process by which luminous energy distributions attributable to the undistorted pattern, i.e. one created without a windscreen, are removed from the transform of the distorted pattern. For instance, if the spread function defining the Fraunhofer diffraction pattern for an undistorted photographed pattern is deconvolved with the transform of the distorted pattern, the result yields the windscreen distortion effects alone.

Figure 7:
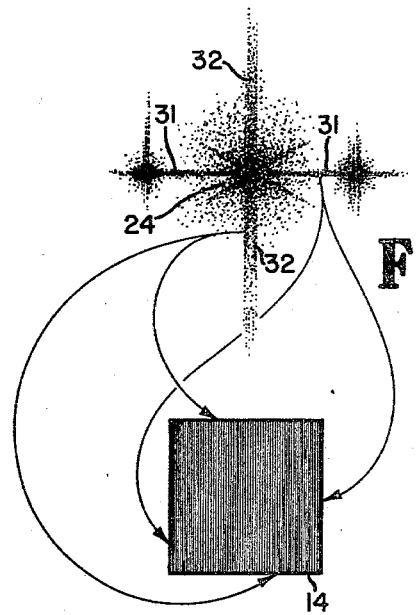
FIG. 7 schematically relates the extraneous projections appearing in the Fraunhofer diffraction pattern to the borders of the transparency undergoing optical transformation.

Center point 24 of the transformed pattern appearing in FIG. 6, and other adjacent points, actually exhibit extraneous projections. Normally their effect is minimal, though in limited cases they may disguise the exact location or shape of points 18. Reference to FIG. 7 provides an understanding of their cause, effect and suppression. The figure only shows center point 24, and the two points either side thereof, in that the projections attenuate rapidly thereafter. As implied by the dashed linking lines, left/right projections 31 are attributable to abrupt terminations of the pattern at the right and left borders of transparency 14, while top/bottom projections 32 are the product of the top and bottom transparency borders. Alterations in the pattern will undoubtedly alter the size and shape of these projections. Generally, if luminous energy beam 13 is smaller than transparency 14 the projections are suppressed.

The vertical bar pattern shown in and described with reference to FIGS. 1 and 2 may be rotated by 90 degrees to analyze the distortion characteristics in the opposite, horizontal plane. No less contemplated are orientations other than the vertical and horizontal. Furthermore, the invention fully contemplates variations in the patterns, and the structures and methods by which the patterns are recorded, as long as the central feature encompasses an optical Fourier transformation into a domain where distortion characteristics appear as readily quantifiable tangential and radial excursions of that pattern.

I claim:

1. A method for measurement of distortion in a large area of an optically transparent medium, such as an aircraft windscreen, comprising the steps of:
   a. placing a large, high contrast, proportionately distributed bar pattern of alternate dark and light bars on one side of said transparent medium;
   b. making a small, transparency recording of an image of said large bar pattern through said transparent medium;
   c. projecting a beam of coherent luminous energy through said image of the pattern in said transparency recording and focusing the energy passing therethrough so as to produce a Fraunhofer diffraction plane pattern composed of a row of points of light; and
   d. quantitatively evaluating the distortion characteristics of the transparent medium appearing in said Fraunhofer diffraction plane pattern on the basis of location, shape and intensity distribution of said points of light.

2. An apparatus for measurement of distortion in a large area of an optically transparent medium, such as an aircraft windscreen, comprising:
   a. a small transparency film having recorded thereon an image of a large bar pattern of alternate dark and light bars as viewed through said large area of said transparent medium and distorted, if at all, by the effects of said transparent medium;
   b. means for projecting a beam of coherent luminous energy broad enough to illuminate said bar pattern image on said thin transparency film; and c. means for focusing said beam of coherent luminous energy so as to produce a Fraunhofer diffraction plane pattern after the beam has passed through said film, said Fraunhofer diffraction pattern being the Fourier transform of said bar pattern image and composed of a row of points of light wherein the shape and distribution characteristics of said points present the parameters of overall distortion in said transparent medium in a form which is readily amenable to quantification comparison so as to facilitate a pass or fail determination of the optical quality of said medium in terms of distortion.

3. The distortion measurement apparatus as recited in claim 2, wherein said alternate dark and light bars of said large bar pattern have consistency in their relative size and are photographically recorded in said film.

4. The distortion measurement apparatus as recited in claim 2 or 3, wherein the distortion characteristics of said transparent medium appears as quantifiable radial and tangential displacements of said points of light comprising said Fraunhofer diffraction plane pattern.

* * * * *

UNITED STATES PATENT AND TRADEMARK OFFICE
CERTIFICATE OF CORRECTION

PATENT NO. : 4,299,482
DATED : November 10, 1981
INVENTOR(S) : Harry L. Task

It is certified that error appears in the above-identified patent and that said Letters Patent are hereby corrected as shown below:

Col 5, line 10 (claim 2, part c) after "quantification"

add ---and---.

Signed and Sealed this

Ninth Day of March 1982

[SEAL]

Attest:

GERALD J. MOSSINGHOFF

Attesting Officer

Commissioner of Patents and Trademarks